United States Patent [19]

Koontz

[11] 4,397,740

[45] Aug. 9, 1983

[54] METHOD AND APPARATUS FOR COOLING THERMALLY CRACKED HYDROCARBON GASES

[75] Inventor: Stephen L. Koontz, Angleton, Tex.

[73] Assignee: Phillips Petroleum Company, Bartlesville, Okla.

[21] Appl. No.: 429,717

[22] Filed: Sep. 30, 1982

[51] Int. Cl.³ .......................... F28F 19/00; C07C 4/04
[52] U.S. Cl. .................................. 208/48Q; 585/950; 585/650; 422/201; 165/146; 165/174; 208/130
[58] Field of Search .......................... 208/48 R, 48 Q; 585/950; 165/174, 146; 196/98; 422/197, 201, 204

[56] References Cited

U.S. PATENT DOCUMENTS

| 1,725,322 | 8/1929 | Vezie | |
|---|---|---|---|
| 3,081,823 | 3/1963 | Constantikes | 165/32 |
| 3,552,487 | 1/1971 | Tokumitsu et al. | 208/48 Q |
| 3,682,241 | 8/1972 | Clauss et al. | 208/48 Q |
| 3,764,634 | 10/1973 | Ozawa et al. | 422/197 |
| 4,097,544 | 6/1978 | Hengstebeck | 260/683 R |
| 4,151,217 | 4/1979 | Amano et al. | 260/683 R |

Primary Examiner—Delbert E. Gantz
Assistant Examiner—Anthony McFarlane

[57] ABSTRACT

The flow of cracked gases, for example, from an ethylene plant through the tubes of a transfer line heat exchanger is equalized by employing larger cross-section tubes in the outer portion of the exchanger and smaller cross-section tubes in the inner portion of the exchanger thereby preventing, or substantially minimizing, build-up of coke deposits in the exchanger, especially in the inlets of the tubes in the outer portion where coke formation conventionally occurs.

13 Claims, 3 Drawing Figures

(PRIOR)

METHOD AND APPARATUS FOR COOLING THERMALLY CRACKED HYDROCARBON GASES

THE INVENTION

This invention relates to a method of manufacturing olefins by pyrolyzing gaseous hydrocarbons or liquid hydrocarbons followed by cooling of the high temperature cracked gases. In accordance with another aspect, this invention relates to improved methods of quenching high temperature, cracked gases obtained by pyrolysis of gaseous or liquid hydrocarbons by means of an indirect shell-tube heat exchanger known as a transfer line exchanger (TLE). In accordance with another aspect, this invention relates to the cooling of cracked gases in an indirect heat exchanger in a manner such that deposition of coke is substantially minimized, and in some instances, prevented. In accordance with another aspect, this invention relates to an indirect shell-tube heat exchanger containing a plurality of tubes, wherein the tubes are so-arranged and so-sized that coke deposition is minimized or prevented.

BACKGROUND

Thermal cracking of gaseous and liquid hydrocarbons to produce lighter weight materials such as olefins is well-known. In addition, the prior art has taught various methods for cooling high temperature gases produced in cracking furnaces. The cracked gases can be cooled either directly, by being quenched by a coolant, or indirectly, by passage through an indirect heat exchange zone, or can be partially cooled by direct cooling followed by indirect cooling. Although the indirect cooling method offers some advantages over the direct cooling method (the direct method adding, usually, extraneous material to the stream being cooled), the indirect cooling system does not prevent occurrence of coking in the path from the outlet of the pyrolysis reaction effluent conduit to the entrance of the indirect cooling device where the cracked gas will be cooled. The present invention is directed to an indirect heat exchange system wherein different sized tubes are used and are so-arranged that the flow of gases through all of the heat exchange tube in the indirect heat exchanger is substantially equalized, thereby preventing build-up of coke deposits at the inlets to the heat exchange tubes.

Accordingly, an object of this invention is to provide an improved heat transfer system wherein deposition of coke is minimized.

Another object of this invention is to provide a method of indirect cooling cracked gases whereby coke deposits in the heat exchanger are minimized.

A further object of this invention is to provide a method of pyrolyzing hydrocarbon feeds and cooling of the pyrolysis effluent in an indirect shell-tube heat exchange zone having a novel arrangement of tubular elements.

Other objects, aspects, as well as the several advantages of the invention will be apparent to those skilled in the art upon reading the specification, the drawings, and the appended claims.

SUMMARY OF THE INVENTION

In accordance with the invention, high temperature gases, such as obtained from a pyrolysis reactor, are cooled with a minimum of coke deposition in a multitubular, indirect cooling heat exchanger wherein the rate of flow of gases through the tubes is equalized by providing a plurality of tubes in the central portion of the heat exchanger having a smaller cross-sectional area than the larger cross-sectional area tubes in the peripheral section surrounding the smaller tubes.

In one embodiment, the flow of cracked gases from a pyrolysis furnace, for example, an ethylene plant, through the tubes of a transfer line indirect exchanger (TLE) is equalized by employing larger cross-section tubes in an outer, or annular, or peripheral portion of the TLE and smaller cross-section tubes in the inner a central portion of the TLE which prevents excessive coking of the outer portion at the inlet tube sheet, thereby allowing longer onstream time for the TLE.

DETAILED DESCRIPTION AND DRAWINGS

Figure 1:
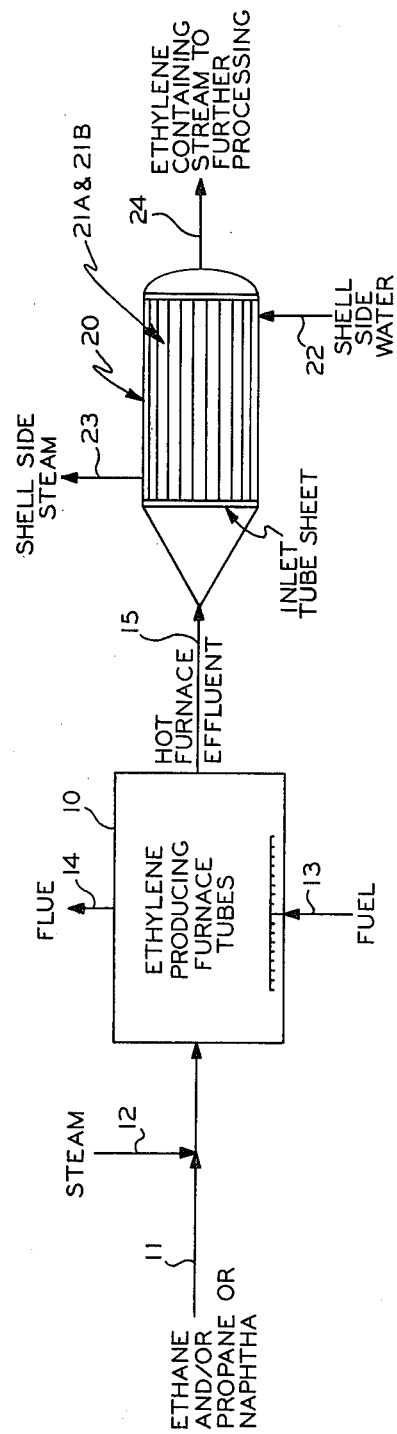
Figure 2:
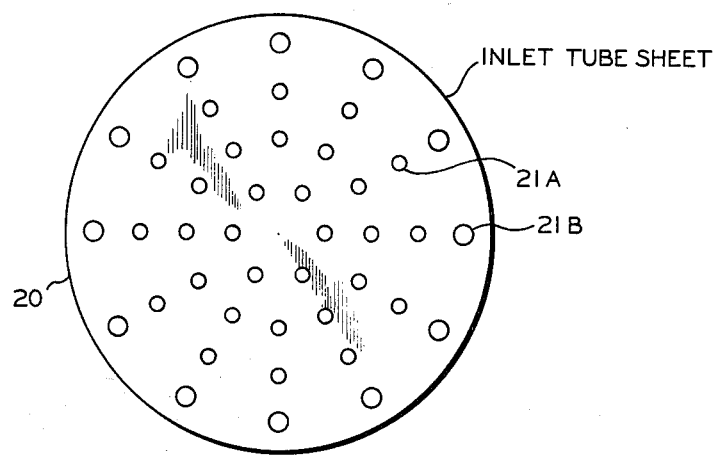
Figure 3:
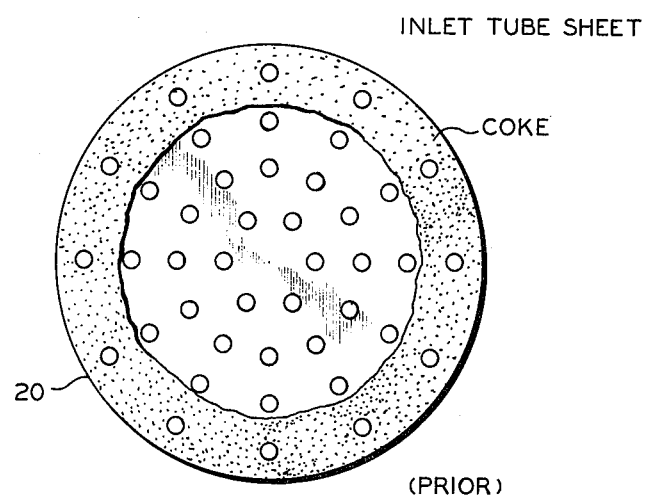

The present invention will now be described by the detailed description and accompanying drawings in which FIG. 1 is an overall flow embodying a cracking furnace to produce ethylene fluid which is indirectly cooled by a transfer line exchanger of the invention;

FIG. 2 is a cross-sectional view of the transfer line exchanger of the invention having outer tubes with a larger diameter than the inner tubes; and FIG. 3 is a cross-sectional view of a conventional or prior art transfer line exchange wherein all of the heat exchange tubes have the same diameter.

Referring now to FIG. 1, a hydrocarbon feed to be cracked such as ethane and/or propane or higher boiling hydrocarbons such as naphthas in line 11 is mixed with steam in line 12 and the mixture introduced into cracking furnace 10. Within cracking furnace 10, the hydrocarbon feed, together with steam, is subjected to pyrolysis conditions to crack the hydrocarbons to lower boiling olefins which are removed from the furnace by way of line 15. Heat is provided to furnace 10 by means of fuel introduced by line 13 which is burned and the combustion gases are removed by means of flue 14.

The thermal conditions existing in furnace 10 can vary somewhat depending upon the particular hydrocarbon feed being subjected to pyrolysis. Generally, however, the cracking temperatures will range from about 1300° F. to about 1650° F., usually at a pressure of about 5 to 50 psia.

The hot furnace effluent in line 15 is passed without direct cooling as quickly as possible to the inlet of transfer line exchanger 20. The cracked gases are passed through heat exchanger 20 and indirectly heat exchanged with a heat exchange fluid surrounding the tubes, such as water, introduced by line 22 and removed as steam from the exchanger by line 23. The cooled, cracked gases are removed from exchanger 20 by line 24 and passed to further processing as desired. The cracked gases passed through exchanger 20 are ordinarily cooled to a temperature about 500° F. to about 800° F.

Referring now to FIG. 2, smaller diameter tubes 21a are arranged in an inner portion of the transfer line exchanger 20 with larger diameter tubes 21b being arranged in the outer portion of the exchanger near the periphery of exchanger 20, and surrounding the smaller tubes 21A. The overall flow area provided by the tubes in exchanger 20 according to the invention will be approximately the same as if all of the tubes were the same size as employed in the prior heat exchanger shown in FIG. 3.

The heat exchanger of my invention uses increased internal diameter tubes in the outer or peripheral portion of the exchanger, e.g., about 15 to about 35 percent of the total tubes, and uses decreased internal diameter tubes in the inner portion of the exchanger, e.g., about 85 to about 65 percent of the total tubes. The internal diameters of the now larger tubes and the internal diameters of the now smaller tubes are selected so that the total cross-sectional flow area through the tubes is substantially the same as the cross-sectional flow area of the original exchanger having all tubes of the same internal diameters. The ratios of the internal diameters of the now larger tubes to the internal diameters of the now smaller tubes is usually in the range of about 1.3 to about 1.6, depending upon the number of the now larger and the now smaller tubes used. The total cross-sectional flow area in the central portion is about 95 percent to about 290 percent of the total cross-sectional flow area in the annular or peripheral portion of the exchanger.

The number of tubes provided in exchanger 20 of the invention (FIG. 2) in the inner portion and the outer portion of the exchanger can vary somewhat depending upon the cross-sectional area of the different sized tubes and whether there is uniformity of cross-sectional area for the individual tubes, and whether the tubes are of uniform cross-sectional area throughout the length of the heat exchanger. In any event, the important consideration is to equalize the flow of gases through the heat exchanger tubes so that the rate of flow of gases through each of the tubes is substantially the same. By so operating, coke deposition can be minimized or even prevented.

In actual operation using the prior TLE, coke is deposited on outer portion (see FIG. 3) of the inlet tube sheet, further cutting down on flow through the outer or peripheral tubes. This coke deposition occurs because the flow of hot cracked gases from the ethylene manufacturing furnace sees all heat exchange tubes of the same internal diameters, with more rapid flow through the centrally positioned tubes and less flow through the tubes adjacent the inner periphery of the inlet to the exchanger.

It is well known in fluid flow that in a conduit the flow is at higher velocity at the center of the conduit and slower at the inner periphery of the conduit.

With hot cracked gases containing not only the desired ethylene product, but also containing heavier highly unsaturated coke-forming hydrocarbons, with both time and temperature these heavier components are formed into coke. Since in the prior operation the flow rate is relatively low at the periphery of the inlet to the tubes (as above commented on), the time that the coke formers are at this peripheral locus is relatively long (as compared with the time the coke formers are at the central locus of the inlet tube sheet, where the flow rate is relatively fast), and since this time is relatively longer at the peripheral area of the inlet tube sheet, there is more coke deposited at this locus than at the central locus of the inlet tube sheet. Ultimately, the tubes at the periphery are clogged with coke at their entries and the unit has to be shut down for coke clean out, so that the proper cooling of the gases from the ethylene plant can be effected.

With this invention, having larger diameter tubes at the periphery of the inlet tube sheet and smaller diameter tubes in the central locus, and using the same rate of flow of ethylene plant effluent hot gases through the same total cross-sectional tube area as in the prior operation, the flow rates of the hot gases at the periphery and at the central locus of the inlet tube sheet are more nearly equalized, decreasing excessive times at any locus of the tube sheet and thereby decreasing coke deposits on the inlet tube sheet, resulting in longer on-stream time with the TLE of the invention than with the TLE of the prior operation.

Coking increases with gas residence time at a locus (assuming the same locus temperature). The invention decreases the time for coking at the peripheral locus because of the increased flow rate at this peripheral locus, due to the larger diameter tubes used at this peripheral locus as compared with the prior operation. The prior operation will have a higher flow rate at the central locus than does the invention, because the prior TLE has a lower flow rate at its periphery than the invention (flowing the same total rate of gas in each operation).

There is no "wall drag" at the central locus, and even with the somewhat lower flow rate at the central locus of the invention, residence time increase for coke deposition is of only a minor amount.

Even if coking occurs in the invention, the coking is not concentrated at the peripheral tubes with resulting clogging as in the prior TLE, but the coking is spread out throughout the tube sheet and longer on-steam time for the invention TLE is realized.

EXAMPLE

| Transfer Line Shell-Tube Boilers | | |
|---|---|---|
| Total Tube Flow, SCF/Hr., | | 417,500 |
| Inlet Temperature, °F., | | 1,535 |
| Inlet Pressure, PSIG., | | 14 |
| | Prior Way | Invention Way |
| Tubes: | | |
| Total Number | 103 | 103 |
| Outer 26 I.D., inches, | 1.5 | 2 (increased) |
| Inner 77 I.D., inches, | 1.5 | 1.3 (decreased) |
| Increased Peripheral Area, %, | 0 | +78 |
| Decreased Inner Area, %, | 0 | −25 |
| Coke at Peripheral Area of Inlet Tube Sheet | Yes | Minimize |
| Extra On-stream Time, Est %, | 0 | +20 |

The total tube flow cross-sectional areas in both the prior exchanger (FIG. 3) and in the invention exchanger (FIG. 2) calculated to be about the same at 182 square inches. However, the invention's cross-sectional flow area in the outer or peripheral 26 tubes is about 78 percent more than the cross-sectional flow area of the prior exchanger at this time locus. This larger flow area at this peripheral locus of the invention minimizes low flow of cracked gases at this locus, and thereby minimizes coking at this locus, which was found with the operation of the prior exchanger, with an extimated 20 percent additional on-stream time with the exchanger of the invention.

I claim:

1. A method for minimizing a formation of coke during cooling of a thermally cracked hydrocarbon stream in a shell-tube heat exchange zone which comprises passing a thermally cracked hydrocarbon stream through a plurality of tubular flow paths surrounded by a heat exchange fluid in the shell portion of said heat exchange zone, equalizing the rate of flow of said stream through the flow paths in said heat exchanger by providing a plurality of flow paths in a central portion of said heat exchanger with each of said flow paths having a smaller cross-sectional area than the flow paths in an annular or peripheral section surrounding the flow paths in the central portion, and thereby minimizing the amount of coke deposition in said heat exchange zone.

2. A method according to claim 1 wherein the total cross-sectional area for the flow paths in the central portion of said heat exchange zone is about 95 to 290%, the total cross-sectional area of the flow paths in the said annular or peripheral section.

3. A method according to claim 1 wherein the total number of flow paths in said central portion of said heat exchange zone comprises about 65 to about 85 percent of the total tubes and the total number of flow paths in said annular or peripheral section comprises about 35 to about 15 percent of the total number of flow paths.

4. A method according to claim 3 wherein the individual flow paths in said central portion and said annular section are of substantially uniform cross-sectional area throughout the length of each of the flow paths.

5. A method according to claim 1 wherein the number of flow paths in said central portion is approximately 80 with each having an inner diameter of about 1.3 inches and the number of flow paths in the annular or peripheral section is about 25 with each having an inner diameter of about 2 inches.

6. A method of cracking hydrocarbons to produce a gaseous cracked product with a minimum of coke formation during quenching or cooling which comprises cracking a hydrocarbon feed at an elevated temperature to produce a gaseous cracked product comprising olefins and coke-forming hydrocarbons, cooling the gaseous cracked product by passing it through a multi-tubular transfer line exchanger in indirect heat exchange relationship with a heat exchange fluid wherein the tubular flow paths positioned in the central or core portion of said transfer line exchanger are of smaller cross-section area than the outer flow paths arranged in an annular pattern around the tubular flow paths in the central portion of the exchanger so that the rate of flow of gaseous cracked product through all flow paths is about the same, thereby minimizing build-up of coke in the transfer line exchanger.

7. A method according to claim 6 wherein the total cross-sectional area for the flow paths in the central portion of said heat exchange zone is about 95 to 290% the total cross-sectional area of the flow paths in the said annular section.

8. A method according to claim 6 wherein the total number of flow paths in said central portion of said heat exchange zone comprises about 65 to about 85 percent of the total tubes and the total number of flow paths in said annular or peripheral section comprises about 35 to about 15 percent of the total number of flow paths.

9. A method according to claim 8 wherein the individual flow paths in said central portion and said annular section are of substantially uniform cross-sectional area throughout the length of each of the flow paths.

10. A method according to claim 6 wherein the number of flow paths in said central portion is approximately 80 with each having an inner diameter of about 1.3 inches and the number of flow paths in said annular section is about 25 with each having an inner diameter of about 2 inches.

11. A system for cracking hydrocarbons and cooling the cracked effluent with minimum coke deposition in a multi-tubular indirect quench-cooling heat exchanger which comprises:
(a) a furnace for cracking a hydrocarbon feed, said furnace having an inlet pipe for entrance of the hydrocarbon feed to the furnacre and an outlet pipe for removal of gaseous cracked product,
(b) a conduit means connected to said outlet pipe and in open communication with the inlet of a multi-tubular shell-tube indirect heat exchanger,
(c) inlet conduit means and outlet conduit means connected to the shell of said heat exchanger for introduction and withdrawal of heat exchange fluid surrounding the tubes within said heat exchanger,
(d) an outlet pipe connected to said heat exchanger for withdrawal of cooled gaseous product, and
(e) an inlet tube sheet and an outlet tube sheet positioned within said heat exchanger with each tube sheet being connected to a plurality of tubes for passage of gaseous product from said furnace through said heat exchanger in indirect heat exchange relationship with heat exchange fluid in the shell side of said heat exchanger, said tubes being so-sized that the rate of flow of gaseous product throughout each of the tubes is substantially equal and so-arranged that tubes of smaller diameter are positioned within a central portion of said heat exchanger and tubes of larger diameter are positioned in annular section surrounding the tubes in the central portion with the proviso that the total number of tubes in said central portion comprises about 65 to about 85 percent of the total tubes and the number of tubes in the annular section comprises about 35 to about 15 percent of the total number of tubes.

12. A system according to claim 11 wherein the total cross-sectional area for the tubes in the central portion of said heat exchanger is about 95 to about 290 percent of the total cross-sectional area of the flow paths in the annular section.

13. A system according to claim 11 wherein the number of tubes in the central portion is about 80 with each having an inner diameter of about 1.3 inches and the number of tubes in the annular section is about 25 with each having an inner diameter of about 2 inches.

* * * * *